US00PP08536P

United States Patent [19]

Panzer

[11] Patent Number: Plant 8,536

[45] Date of Patent: Jan. 11, 1994

[54] AZALEA — AL PANZER VARIETY

[75] Inventor: Fred Panzer, Beaverton, Oreg.

[73] Assignee: Panzer Nursery, Inc., Beaverton, Oreg.

[21] Appl. No.: 881,738

[22] Filed: May 6, 1992

[51] Int. Cl.[5] ..... A01H 5/00
[52] U.S. Cl. ..... Plt./56
[58] Field of Search ..... Plt. 55–57

[56] References Cited

PUBLICATIONS

Leach, D. G. (Listing) 'Peace', *Rhododendrons of the World* 1961 Charles Serbiner's Sons, New York, p. 482.

*Primary Examiner*—James R. Feyrer
*Attorney, Agent, or Firm*—Chernoff, Vilhauer, McClung & Stenzel

[57] ABSTRACT

A new variety of azalea particularly characterized by its sturdy and generally upright growth habit, tea rose-shaped, red-purple flowers, and its unusually late blooming habit.

2 Drawing Sheets

BACKGROUND OF THE INVENTION

This new variety of florist azalea was discovered in 1987 growing on a potted plant at the inventor's commercial nursery located in Beaverton, Oreg. The new variety is a spontaneous mutation of the "Peace" azalea, discovered as a limb sport. Subsequent asexual propagation by cuttings at the same location has demonstrated that the below-described valuable characteristic is genetically stable and holds true from generation to generation. The Peace azalea is a florist azalea of unknown origin and is known to be available only from a limited number of commercial greenhouses in the Pacific Northwest.

The "Al Panzer" azalea and its parent Peace azalea are identical in all aspects except three.

1. The Peace flower is white compared to the red-purple Al Panzer flower;

2. The young stems of the Peace azalea remain in the yellow-green (group color 114*c*) from the base to the tip, whereas the young stems of the Al Panzer change to a red-purple (group color 59*b*); and 3. The older leaves of the Peace azalea are always green (group color 137*a* or 139*a*), whereas the older leaves of the Al Panzer have a tendency to have a reddish bronze tint under high light or extreme temperature conditions.

The forcing requirements and natural flower dates of the Peace azalea and the Al Panzer azalea are identical. Neither variety has any fragrance. Flower fertility is unknown for either variety. The outdoor reaction for either variety is not known as both varieties are florist azaleas and are always grown in a greenhouse.

DESCRIPTION OF THE PLANT

Figure 1:
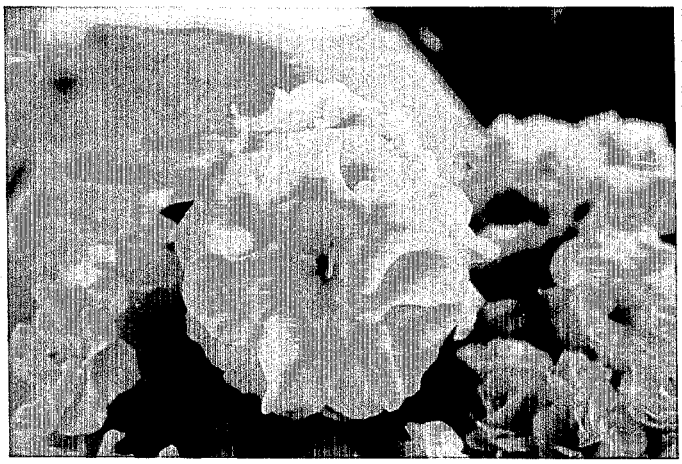
FIG. 1 shows the plant in bloom.
Figure 2:
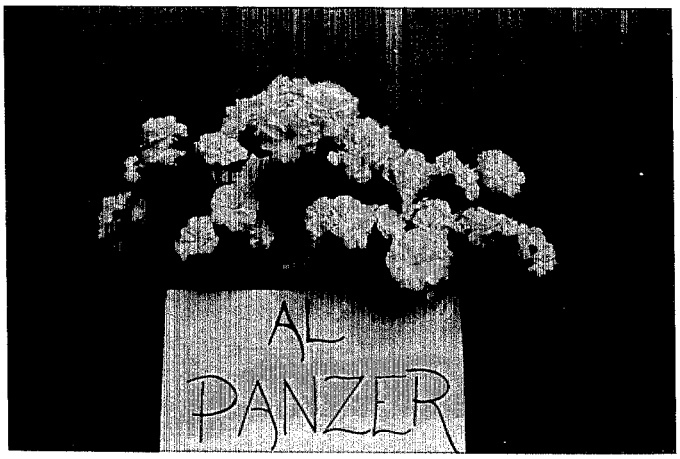
FIG. 2 shows the plant potted.
Figure 3:
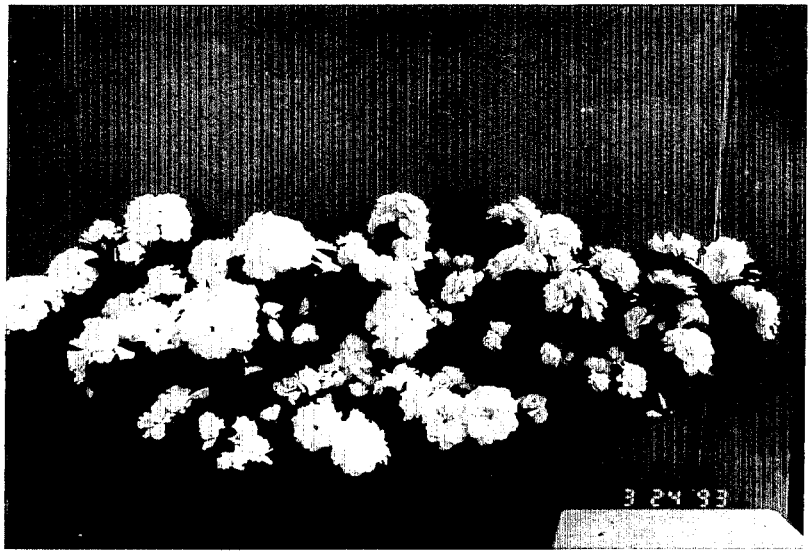
FIG. 3 shows a parent Peace azalea on the left and an Al Panzer azalea on the right.
Figure 4:
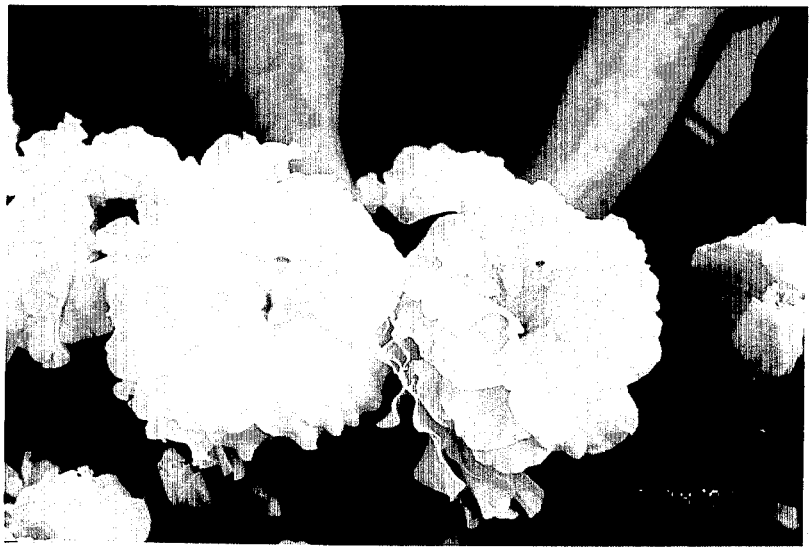
FIG. 4 shows a Peace azalea flower on the left and an Al Panzer azalea flower on the right.

The following is a detailed description of the new azalea variety based upon observations made in greenhouses located at the inventors nursery in Beaverton, Oreg. Where possible, precise color assessment has been made with reference to The Royal Horticulture Society Colour Chart.

Plant

Origin: Peace, origin unknown.

Classification: Botanical.

*Family.*—Ericaceae.

*Genus.*—Rhododendron.

*Species.*—Unknown.

*Cultivar.*—Al Panzer.

*Commercial.*—Hybrid azalea.

*Market class.*—Florist azalea.

Form: Upright to spreading bush.

Height: Medium, 7 inches to 9 inches.

Growth: Medium grower, sturdy and generally upright.

Branching: Well-branched, with prolific branching tendencies.

Stem: Younger shoot color is distinctive of this variety, the base is yellow green group #144C and the tip is red-purple group #59B; older stems are a woody bronze color.

Foliage: Abundant, generally alternate similar to the Helmut Vogel azalea. Evergreen, foliage is retained through the year.

*Leaf size.*—¾"–1" Across, 1"–2" from base to apex, petiole approximately ¼" long.

*Leaf shape.*—Elliptic to oblanceolate and entire with a mucronate apex and an obtuse base.

*Texture.*—Slightly pubescent.

*Aspect.*—Glossy.

*Ribs and veins.*—Alternately pinnate.

*Color.*—Upper side — Young leaves: Yellow green group #144A. Older leaves: Green group #137A or 139A (older leaves may have a reddish or bronze tint under high light or high temperature conditions). Under side — Young leaves: Yellow green group #144B. Older leaves: Green group #138A or 138B.

Bud:

*Form.*—Ovate and pointed.

*Size.*—¼"–¾" *long,* ¼"–½" *diameter.*

*Opening rate.*—Buds open slowly.

*Opening bud color.*—When sepals first divide — Red group #36C or #38C with white variegation #155D. When petals begin to unfurl — Red-purple group #68D or #73C with white variegation #155D.

*Sepals color.*—When tight bud — Yellow green #154C or #154D with pink blush.

*Calyx.*—Funnel-shaped with deep clefts, small, and pubescent.

*Peduncel.*—Yellow green #144B, strong and upright, ¼"-½" long, and pubescent.

Flower:

*Blooming habit.*—Naturally a late-season azalea.

*Size.*—About 2"-2½" in diameter and about 1" in depth, the flower flattens out as it opens.

*Shape.*—Tea rose shape.

*Inflorescence.*—Umbel, in clusters of 2-6 flowers.

*Petals.*—Multi-petaled, usually in groups of five. Arrangement: Imbricated petals, double flowers with three-ten corollas that overlap alternately. Form: Corolla generally gamopetalous; fused at the base. Texture: Soft and delicate. Aspect: Intense, semi-glossy. Color: Petals — red-purple group #68D or #73C with the splotches in the throat #61C and the margin #155D. The flower fades to #56C or #56D.

*Peduncle.*—Yellow-green #144B, strong and upright, ¼"-½" long, and pubescent.

*Persistence.*—Flowers last for over a month, hang on and dry.

*Reproductive organs.*—Pistil usually single, ovary superior and hairy, stamens usually not present.

Disease tolerance: Very disease resistant.

Hardiness: Estimated hardy to 25° to 30°.

What is claimed is:

1. A new and distinct azalea, referred to by the cultivar designation Al Panzer, substantially as herein shown and described, characterized particularly by its sturdy and generally upright growth habit, tea rose-shaped, red-purple flowers, and its late blooming habit.

* * * * *